(12) United States Patent
Risi et al.

(10) Patent No.: US 8,249,724 B2
(45) Date of Patent: Aug. 21, 2012

(54) ELONGATE IMPLANTABLE CARRIER MEMBER HAVING AN EMBEDDED STIFFENER

(75) Inventors: Frank Risi, Newtown (AU); Godofredo Timbol, Harris Park (AU)

(73) Assignee: Cochlear Limited, Macquarie University, NSW (AU)

( * ) Notice: Subject to any disclaimer, the term of this patent is extended or adjusted under 35 U.S.C. 154(b) by 863 days.

(21) Appl. No.: 12/065,209

(22) PCT Filed: Aug. 31, 2006

(86) PCT No.: PCT/US2006/034010
§ 371 (c)(1),
(2), (4) Date: Oct. 14, 2008

(87) PCT Pub. No.: WO2007/027879
PCT Pub. Date: Mar. 8, 2007

(65) Prior Publication Data
US 2009/0030483 A1    Jan. 29, 2009

(30) Foreign Application Priority Data
Aug. 31, 2005  (AU) ............................... 2005904743

(51) Int. Cl.
*A61N 1/00* (2006.01)
*A61B 5/04* (2006.01)

(52) U.S. Cl. ............ 607/137; 607/55; 607/56; 607/115; 600/379

(58) Field of Classification Search ............. 607/55–56, 607/115, 137; 600/379
See application file for complete search history.

(56) References Cited

U.S. PATENT DOCUMENTS

| 5,545,219 | A | 8/1996 | Kuzma |
| 6,074,422 | A | 6/2000 | Berrang et al. |
| 2003/0045921 | A1 * | 3/2003 | Dadd et al. ................... 607/137 |
| 2004/0122501 | A1 * | 6/2004 | Dadd et al. ................... 607/137 |

OTHER PUBLICATIONS

International Search Report. PCT/US06/34010. Mailed Feb. 5, 2007.

* cited by examiner

*Primary Examiner* — Nicole F Lavert
(74) *Attorney, Agent, or Firm* — Kilpatrick, Townsend & Stockton, LLP.

(57) ABSTRACT

An apparatus including a flexible elongate carrier member configured to introduce a therapeutic element into the recipient and a stiffening member, permanently embedded in and longitudinally extending through at least a first region of said carrier member, configured to decrease said flexibility of said carrier member region so as to prevent deformation of said first region during implantation into the recipient.

39 Claims, 5 Drawing Sheets

ELONGATE IMPLANTABLE CARRIER MEMBER HAVING AN EMBEDDED STIFFENER

CROSS-REFERENCE TO RELATED APPLICATIONS

This application claims priority from AU Provisional Application 2005904743, entitled, "A Cochlear Implant Electrode Array," filed Aug. 31, 2005, and U.S. Provisional Patent Application No. 60/748,273, entitled "Electrode Carrier Member Having An Embedded Stiffener for a Prosthetic Hearing Implant," filed Dec. 8, 2005, which are hereby incorporated by reference herein.

BACKGROUND

1. Field of the Invention

The present invention relates generally to stimulating medical devices and, more particularly, to an elongate implantable carrier member having an embedded stiffener.

2. Related Art

Hearing loss is generally of two types, namely conductive and sensorineural. Conductive hearing loss occurs when the normal mechanical pathways for delivering sound to the hair cells in the cochlea are impeded, for example, by damage to the ossicles. In such cases, hearing loss may often be improved by the use of conventional hearing aids, which amplify sound so that acoustic information reaches the cochlea and the hair cells. Such hearing aids utilize acoustic mechanical stimulation whereby sound is amplified according to a number of varying techniques, and delivered to the inner ear as mechanical energy. This may be through a column of air applied to the eardrum, or through the delivery of direct mechanical forces to the ossicles of the middle ear.

Sensorineural hearing loss, however, is due to the absence or destruction of the hair cells in the cochlea which are needed to transduce acoustic signals into auditory nerve impulses. Individuals suffering from this type of hearing loss are unable to derive any benefit from conventional hearing aids regardless of the volume of the acoustic stimulus. This is because the natural mechanisms for transducing sound energy into auditory nerve impulses have been damaged. In such cases, Cochlear™ implants (also referred to as Cochlear™ devices, Cochlear™ prostheses, Cochlear™ implant systems, and the like; simply "cochlear implants" herein) have been developed to provide the sensation of hearing to such individuals. In cochlear implants, electrical stimulation is provided via stimulating electrodes positioned as close as possible to the nerve endings of the auditory nerve, essentially bypassing the hair cells in a normally functioning cochlea. The application of a stimulation pattern to the nerve endings causes impulses to be sent to the brain via the auditory nerve, resulting in the brain perceiving the impulses as sound.

The treatment of both of the noted types of hearing loss has been quite different, relying on two quite different principles to deliver signals to be perceived by the brain as sound. It is relatively common in hearing impaired individuals to experience sensorineural hearing loss for sounds in the high frequency range, and yet still be able to discern sounds in the middle to low frequency range, either through the use of a conventional hearing aid, or naturally. Traditionally, in the majority of such cases, the recipient would only receive treatment to preserve and improve the hearing for the middle to low frequency sounds, most probably via a conventional hearing aid, and little would be done to attempt to restore the hearing loss for the high frequency sounds. This is due to the potential trauma caused by the implantation of an electrode assembly into the cochlea. Only if the individual lost the ability to perceive middle to low frequency sounds would consideration then be given to restoring the hearing loss for the high frequency sounds, in which case a cochlear implant would be considered a possible solution.

More recently, there has been an increased interest in Electro-Acoustical Stimulation (EAS) in which electrical stimulation of the cochlea is used in conjunction with acoustical stimulation. This has resulted in the development of various electrode assemblies that are designed to be as atraumatic to residual hearing as possible.

SUMMARY

In one aspect of the present invention an apparatus is disclosed. The apparatus comprises: a flexible elongate carrier member configured to introduce a therapeutic element into the recipient; and a stiffening member, permanently embedded in and longitudinally extending through at least a first region of said carrier member, configured to decrease said flexibility of said carrier member region so as to prevent deformation of said first region during implantation into the recipient. The apparatus may be an electrode assembly for implanting electrodes in the recipient's cochlea.

In another aspect of the present invention, a cochlear implant is disclosed. The cochlear implant comprises: a speech processor for processing received sounds to generate coded stimulation control signals; a stimulator unit configured to generate stimulation signals in response to said control signals; and an electrode assembly. The electrode assembly in turn comprises: a flexible elongate carrier member having a plurality of electrodes disposed on thereon, said electrodes configured to stimulate auditory nerves of the recipient's cochlea; and a stiffening member, permanently embedded in and longitudinally extending through at least a first region of said carrier member, configured to decrease said flexibility of said carrier member region so as to prevent deformation of said first region during implantation into the recipient.

DETAILED DESCRIPTION

Embodiments of the present invention are generally directed to an apparatus and method for facilitating the temporary or permanent implantation of a therapeutic element into a patient. Embodiments of the present invention are described below in connection with one type of medical device, a cochlear implant. Cochlear implants use direct electrical stimulation of auditory nerve cells to bypass absent or defective hair cells that normally transduce acoustic vibrations into neural activity. Such devices generally use electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, the cochlear implant provides stimulation of the cochlear nucleus in the brainstem.

Exemplary embodiments of the present invention are described herein in conjunction with a exemplary cochlear implant such as a Contour™, Freedom™, Nucleus™ or Cochlear™ implant sold by Cochlear Limited, Australia. Such devices are described in U.S. Pat. Nos. 4,532,930, 6,537,200, 6,565,503, 6,575,894, and 6,697,674, which are hereby incorporated by reference herein. It should be understood to those of ordinary skill in the art that embodiments of the present invention may be used in other stimulating medical devices such as other types of prosthetic hearing implants, neurostimulators, cardiac pacemakers/defibrillators, etc. as well as other medical devices which utilize an elongate carrier member to temporarily or permanently implant, deliver or otherwise introduce a therapeutic element such as an inert or pharmacological agent, sensor, device, etc., into a recipient.

Figure 1:
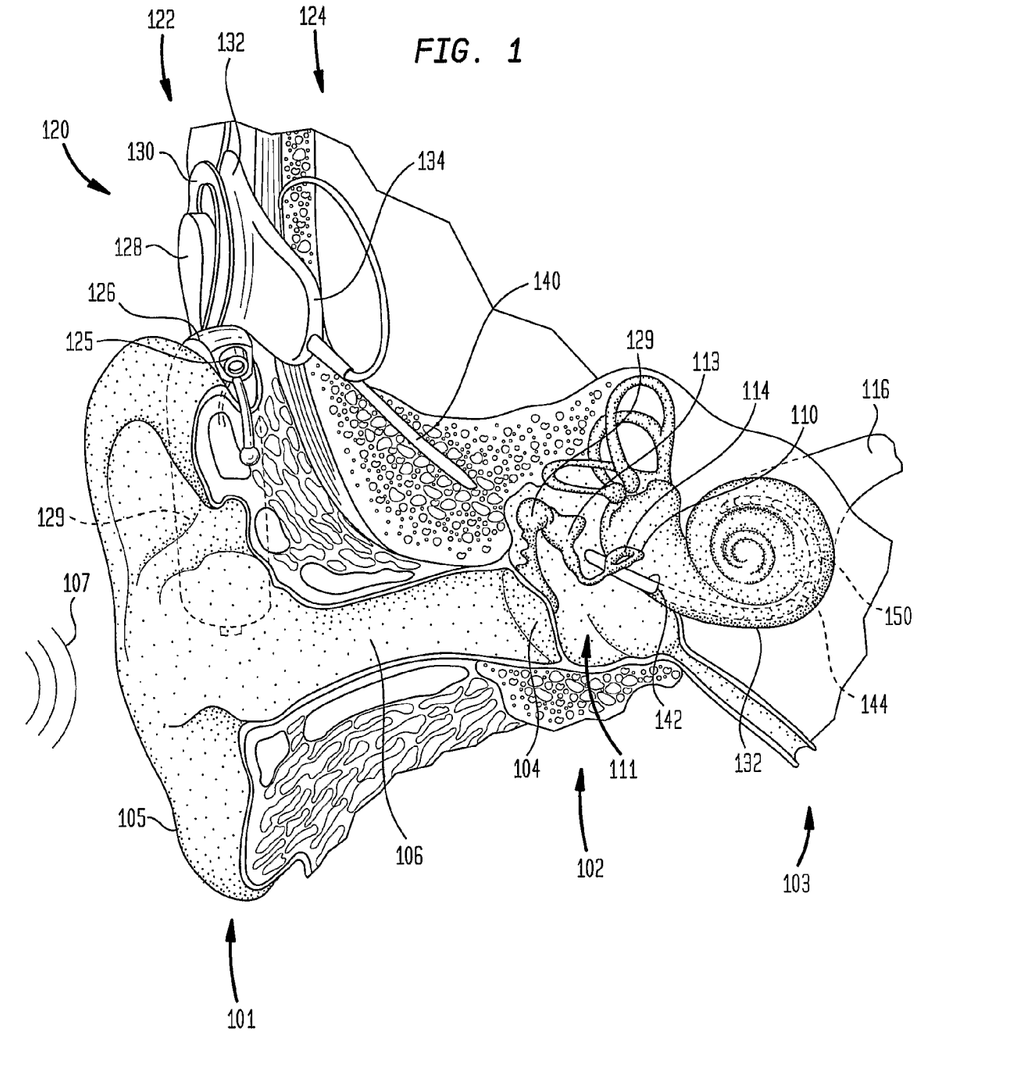
FIG. 1 is a perspective view of an implanted cochlear implant suitable for implementing embodiments of the present invention.

FIG. 1 is a cut-away view of the relevant components of outer ear 101, middle ear 102 and inner ear 103, which are described next below. In a fully functional ear, outer ear 101 comprises an auricle 105 and an ear canal 106. An acoustic pressure or sound wave 107 is collected by auricle 105 and channeled into and through ear canal 106. Disposed across the distal end of ear cannel 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 129 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 132. Such fluid motion, in turn, activates tiny hair cells (not shown) that line the inside of cochlea 132. Activation of the hair cells causes appropriate nerve impulses to be transferred through the spiral ganglion cells and auditory nerve 116 to the brain (not shown), where they are perceived as sound. In persons experiencing sensorineural hearing loss, there is an absence or destruction of the hair cells. Oftentimes, a cochlear implant is utilized to directly stimulate the spinal ganglion cells to provide a hearing sensation to such persons.

FIG. 1 also shows how an exemplary cochlear implant 120 is positioned in relation to outer ear 101, middle ear 102 and inner ear 103. Prosthetic hearing implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is outputted to a BTE (Behind-The-Ear) speech processing unit 126. During use, microphone 125 is preferably worn on the pinna of the recipient, however, other suitable locations may be envisaged, such as a lapel of the recipient's clothing. Speech processing unit 126 generates coded signals which are provided to an external transmitter unit 128, along with power from a power source such as a battery.

External transmitter unit 128 comprises an external coil 130 and, preferably, a magnet (not shown) secured directly or indirectly in external coil 130. Internal components 124 comprise an internal receiver unit 132 having an internal coil (not shown) that receives and transmits power and coded signals from external assembly 122 to a stimulator unit 134 to apply the coded signal along an electrode assembly 140. Electrode assembly 140 enters cochlea 132 at cochleostomy region 142 and has one or more electrodes 150 is positioned to substantially be aligned with portions of tonotopically-mapped cochlea 115. Signals generated by stimulator unit 134 are applied by the electrodes 150 of electrode array 144 to cochlea 132, thereby stimulating auditory nerve 116. It should be appreciated that although in the embodiment shown in FIG. 1 electrodes 150 are arranged in an array 144, other arrangements are possible.

Electrode assembly 140 should assume an optimal electrode position in cochlea 132 upon or immediately following implantation into the cochlea. It is also desirable that electrode assembly 140 be configured such that the insertion process causes minimal trauma to the sensitive structures of the cochlea. Usually an electrode assembly is held in a straight configuration at least during the initial stages of the insertion procedure, conforming to the natural shape of the cochlea during and subsequent to implantation.

While cochlear implant system 100 is described as having external components, in another embodiment, the controller, including the microphone, speech processor and power supply, may also be implantable. In such embodiments, the controller may be contained within a hermetically sealed housing or the housing used for stimulator unit 134.

Figure 2A:
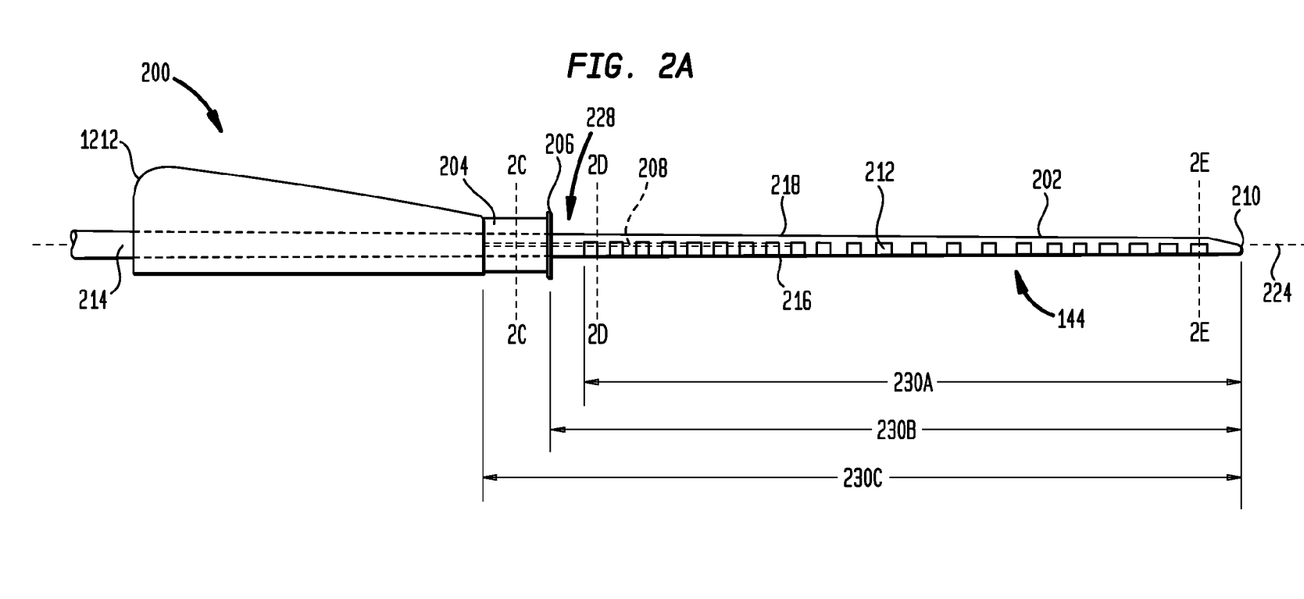
FIG. 2A is a side view of an electrode assembly in accordance with one embodiment of the present invention shown prior to insertion into a cochlea.
Figure 2B:
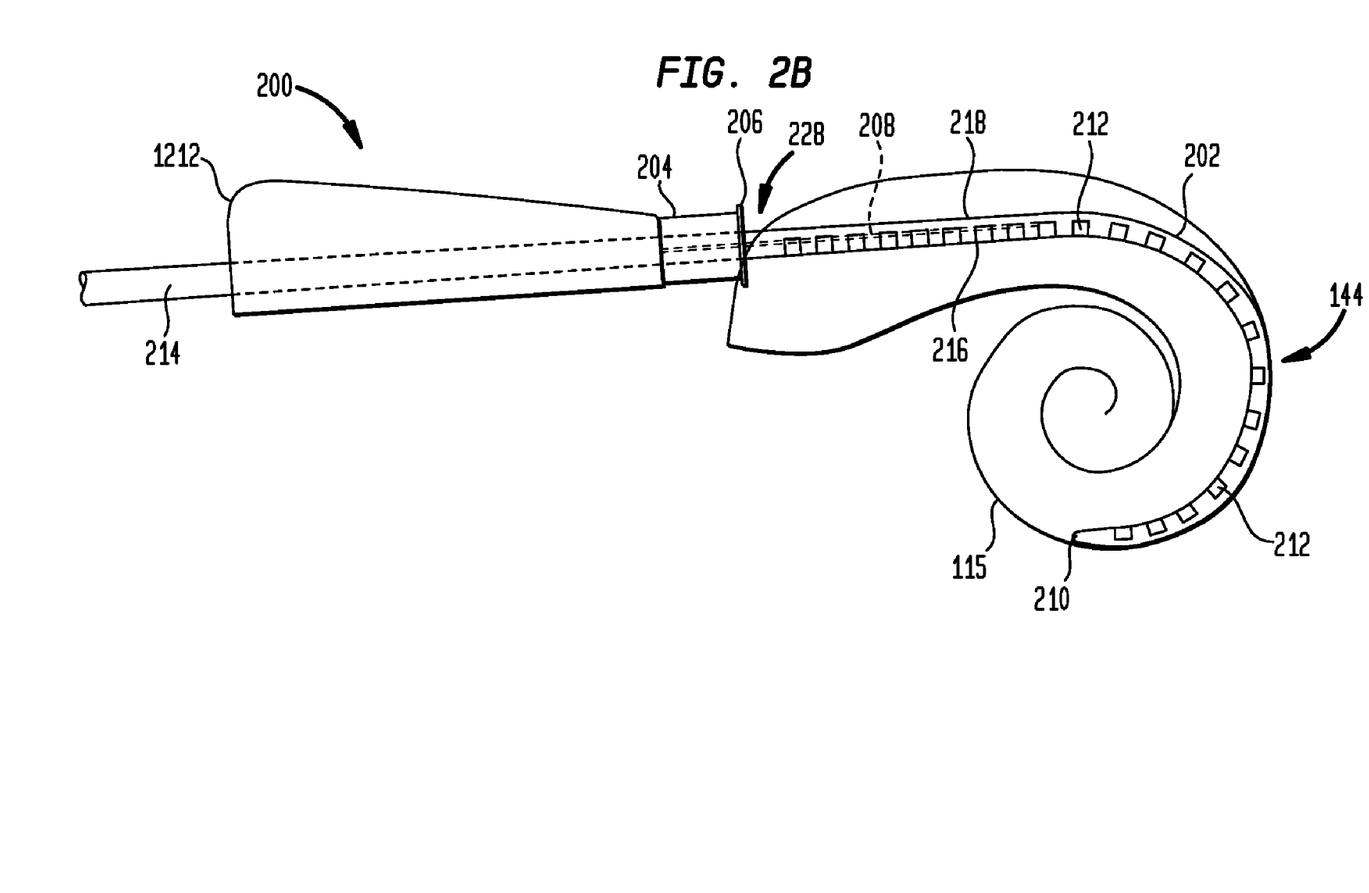
FIG. 2B is a side view of the electrode assembly illustrated in FIG. 2A, shown after insertion into a cochlea.
Figure 2C:
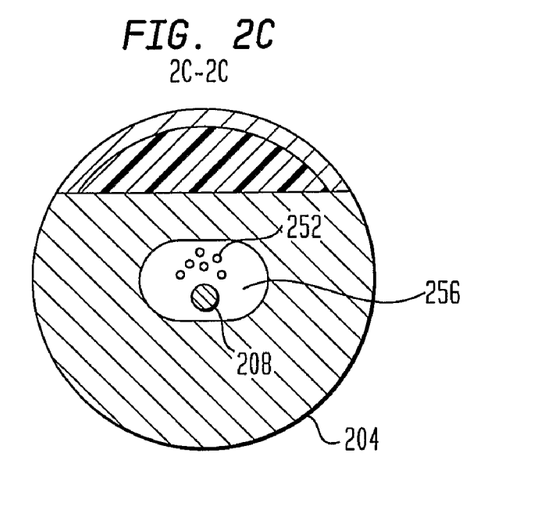
FIG. 2C is a cross sectional view of the electrode assembly of FIGS. 2A and 2B taken along section line 2C-2C in FIG. 2A.
Figure 2D:
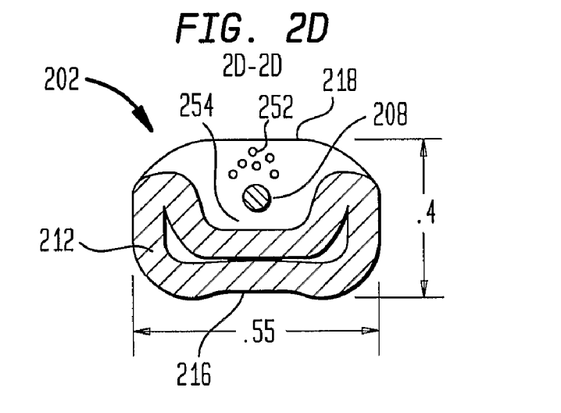
FIG. 2D is a cross sectional view of the electrode assembly of FIGS. 2A and 2B taken along section line 2D-2D in FIG. 2A.
Figure 2E:
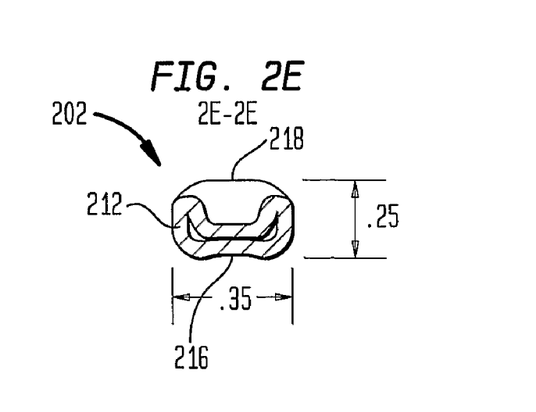
FIG. 2E is a cross sectional view of the electrode assembly of FIGS. 2A and 2B taken along section line 2E-2E in FIG. 2A.

FIG. 2A is a side view of an electrode assembly 200 in accordance with one embodiment of the present invention shown prior to insertion into a cochlea. FIG. 2B is a side view of electrode assembly 200 shown after insertion into a cochlea. FIGS. 2C-2E are cross sectional views of electrode assembly 200 taken along their respective section lines illustrated in FIG. 2A.

Electrode assembly 200 comprises a carrier member 202, a collar member 204, a holding member 1212 and lead 214. Carrier member 202 has a distal end or tip region 210 and a proximal end 228 connected to laterally-extending collar member 204. The opposing end of collar member 204 is connected to holding member 1212. A lead 214 longitudinally extends through carrier member 202, collar member 204 and holding member 1212 to electrically connect electrodes 150 with an external device such as receiver/stimulator unit 134 (FIG. 1).

When implanted in a recipient, the longitudinally-extending surface of carrier member 202 which faces the interior of cochlea 132 is referred to herein as the medial surface 216 of carrier member 202. The opposing side of carrier member 202, referred to herein as lateral surface 218, faces the external wall and bony capsule (not shown) of cochlea 132. It should be understood that the terms medial surface, medial direction and the like are generally used herein to refer to the surfaces, features and directions toward the center of cochlear 132, while the terms lateral surface, lateral direction and the like are generally used herein to refer to surfaces, features and directions toward the exterior of cochlea 132.

A plurality of spaced-apart electrodes 212 are mounted on or in carrier member 202. Electrodes 212 may be disposed in a linear or non-linear array on or in carrier member 202, and may be positioned to align with predetermined regions of tonotopically mapped cochlea 132. In one alternative embodiment, electrodes 212 have variable spacing as described in U.S. Provisional Patent Applications 60/748, 217, 60/748,274, and 60/748,314, which are hereby incorporated by reference herein. Such arrangements allow for individual electrodes 212 to be energized to stimulate selected regions of cochlear 132.

In one embodiment, electrodes 212 are half-band electrodes disposed on medial surface 216 of carrier member 202. It should be appreciated, however, that any electrodes now or later developed suitable for a particular application or therapeutic objective may be used in alternative embodiments of the invention. For example, in one alternative embodiment, electrodes 212 are banded electrodes extending substantially around carrier member 202. In another alternative embodiment, electrodes 212 do not laterally extend to or around the edges of carrier member 202.

Typically, each electrode 212 is arranged orthogonal to longitudinal axis 250 of carrier member 202. It should be appreciated, however, that other relative positioning and orientations may be implemented in alternative embodiments. It should further be appreciated that the quantity of electrodes 212 may vary from as few as one or two to as many as twenty-four or more.

In certain embodiments, at least one electrode 212 has a surface that is at least adjacent medial surface 216 of carrier member 202. Preferably, one or more electrodes 212 has a surface that is collocated with medial surface 216 of carrier member 202. In another embodiment, the surfaces of electrodes 212 are raised above or recessed into medial surface 216 of carrier member 202.

Electrodes 212 may be manufactured from a biocompatible conductive material such as platinum, although other materials or combinations of materials may be used. Alternatively, electrodes 212 may be coated with a biocompatible covering that does not substantially interfere with the transfer of stimulation signals to cochlear 132.

Each electrode 212 is electrically connected to at least one multi- or single-filament wire 252 that is embedded within flexible carrier member 202, collar member 204, handle member 212 and lead 214. As shown in FIG. 2D, in some embodiments wires 252 are embedded in the volumetric core 254 of carrier member 202. In collar member 204, shown in FIG. 2C, stiffening member 208 and wires 252 extend or travel through a central volumetric core 256. In an alternative embodiment, wires 252 may be located at or near surface 216 and/or surface 218 of carrier member 202. In other embodiments, wires 252 are embedded in different regions of carrier member 202 to facilitate attainment of a desired curvature, to maintain orientation of carrier member 202 once it is implanted, to attain a desired level of isolation between stiffening member 208 and wires 252, and/or to achieve other objectives. It is through wires 252 that stimulator/receiver unit 134 (FIG. 1) provides electrical stimuli to electrodes 212. In one embodiment, wires 252 are connected to electrodes 212 by welding, although any suitable connecting means now or later developed may be used.

It should be appreciated that the quantity of wires 252 connected to each electrode 212 may vary. For example, in one alternative embodiment, at least two electrically conducting wires 252 are connected to each of one or more electrodes 212. It should also be appreciated that suitable transmission means other than filament wires may be used to communicably couple receiver/stimulator unit 134 and electrodes 212.

In those embodiments in which stiffening element 208 is electrically conductive, it is insulated from wires 252 and electrodes 212. It should be appreciated, however, that stiffening element 208 may be formed from any materials now or later developed.

Stimulator 134 is preferably encased within a housing that is implantable within the recipient. The housing for the stimulator is commonly implantable within a recess in the bone behind the ear posterior to the mastoid. In one embodiment, lead 214 extends from handle member 212 to stimulator 134 or at least the housing of stimulator 134. In one particular embodiment, lead 214 is continuous; that is, with no electrical connectors required to electrically connect electrode assembly 200 to stimulator 134. One advantage of this arrangement is that there is no requirement for a surgeon implanting electrode assembly 200 to make the necessary electrical connection between wires 252 extending from electrodes 212 and stimulator 134.

Holding member 1212 provides for improved handling, and to identify electrode orientation. As one of ordinary skill in the art would appreciate, in alternative embodiments, holding member 1212 may be configured as described in US Patent Application No 10/825,360, now U.S. Pat. No. 7,349, 744, which is hereby incorporated by reference herein in its entirety.

A profiled tip 210 is implemented in certain embodiments to guide carrier member 202 during the insertion process, and to reduce friction. Alternative embodiments of tip region 210 are described in commonly owned U.S. Provisional Patent Application No. 60/748,217 entitled "Promoting Curvature and Maintaining Orientation In An Electrode Carrier Member Of A Prosthetic Hearing Implant," filed Dec. 8, 2005; U.S. Provisional Patent Application No. 60/748,274 entitled "Electrode Carrier Member For A Prosthetic Hearing Implant Having Optimal Length For Atraumatic Implantation," filed Dec. 8, 2005; and U.S. Provisional Patent Application No. 60/748,317 entitled "Electrode Carrier Member For A Prosthetic Hearing Implant Having Variable Pitch Electrodes To Facilitate Atraumatic Implantation," filed Dec. 8, 2005; all of which are hereby incorporated by reference herein in the entireties. In alternative embodiments, tip region 244 may be as described in U.S. patent application Ser. Nos. 10/825,358, now abandoned, and 11/125,171, now U.S. Pat. No. 7,962, 226, which are hereby incorporated by reference herein in their entireties.

Collar member 204 serves as both a region for grasping electrode assembly 200 and also acts to prevent insertion of carrier member 202 beyond a predetermined maximum depth to reduce the risk of the surgeon over-inserting electrode assembly 200, which could otherwise cause trauma to the delicate structures of cochlea 132. In certain embodiments, the predetermined maximum depth is as described in the above-referenced US Provisional Patent Applications 60/748,217, 60/478,274 and 60/748,317 and U.S. patent application Ser. Nos. 10/518,811 and 11/125,171. Collar member 204 and band 206 are described in further detail in the above applications.

In certain embodiments, carrier member 202 also includes a stiffening member 208 permanently embedded in at least proximal region 228 of carrier member 202. Stiffening member 208 is embedded, for example, during the manufacture of carrier member 202. As shown in FIG. 2A, the illustrative embodiment of stiffening member 208 extends from an extracochlear position through collar member 204 and into carrier member 202. It should be appreciated that in alternative embodiments, stiffening member 208 need not be embedded in collar member 204, and any may longitudinally extend further through carrier member 202 to terminate at any desired location along the length of carrier member 202. As best shown in FIG. 2B, the distance that stiffening member 208 extends into carrier member 202 is such that the stiffening member terminates just before the lateral wall of the first turn of cochlea 132 when carrier member 202 is completely inserted into cochlea 132.

Stiffening member 208 is configured to increase the stiffness of carrier member 202 in the region(s) 202 in which stiffness member 208 is located. As such, stiffening member 208 assists in the prevention of buckling and/or deformation of carrier member 202 in such regions during insertion into cochlea 132. In particular, stiffener member 208 assists in maintaining proximal region 228 of carrier member 202 in a sufficiently straight configuration when subjected to the forces typically experienced during implantation. This allows carrier member 202 and electrodes 212 to be fully implanted into cochlea 132 without being subject to insertion forces that may damage the delicate structures of the cochlea.

Additionally, stiffening member 208 causes electrodes 212 to be positioned closer to the inner wall of cochlea 132, as generally a straight electrode will take a more lateral position in the basal region. As a result, the distance from the stimulating surface of carrier member 202 to the auditory nerve endings is substantially less than would be the case if stiffening element 208 were not embedded in electrode assembly 200. It is anticipated that this will provide similar benefits in the basal region as a perimodiolar electrode, such as the perimodiolar electrode described in U.S. Pat. No. 6,421,569, which is hereby incorporated by reference herein. It should also be appreciated stiffening the stiffness of member 208 may be less than, the same, or greater than the stiffness of carrier member 202, so long as the presence of stiffening member 202 in regions of carrier member 202 results in at least one of such regions having a reduced likelihood of deformation.

Figure 3A:
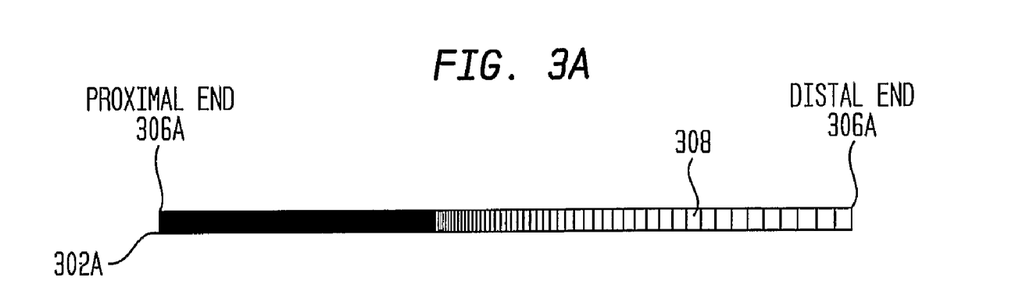
FIG. 3A is a side view of one embodiment of a stiffening element of the present invention suitable for implementation in the carrier member illustrated in FIGS. 2A-2E.
Figure 3B:
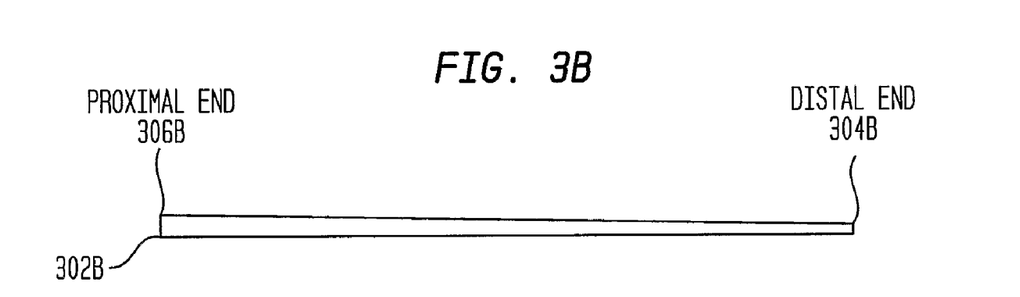
FIG. 3B is a side view of another embodiment of a stiffening element of the present invention suitable for implementation in the carrier member illustrated in FIGS. 2A-2E.
Figure 3C:
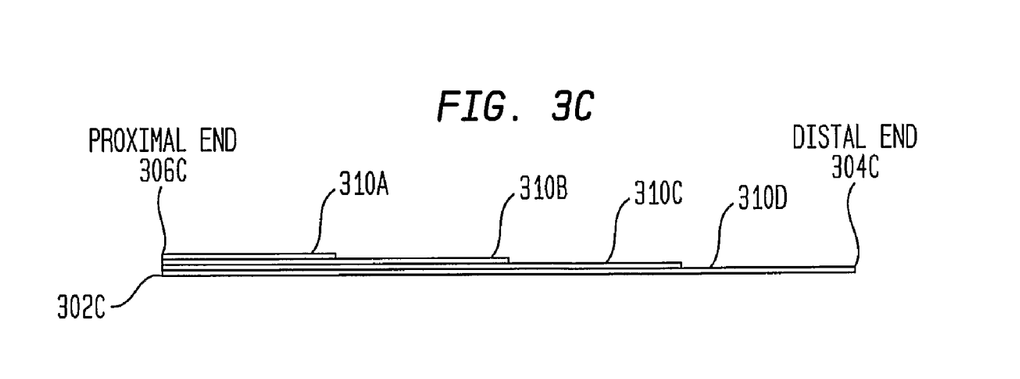
FIG. 3C is a side view of a further embodiment of a stiffening element of the present invention suitable for implementation in the carrier member illustrated in FIGS. 2A-2E.

FIGS. 3A through 3C are side views of different embodiments of stiffening element 218, referred to herein as stiffening element 302A, 302B, and 302C, respectively (generally and collectively referred to as stiffening element 302). Stiffening elements 302 are configured to be embedded in embodiments of electrode assembly 200, as noted above. In these embodiments, the stiffness or malleability of stiffening member 208 is longitudinally varied so that, for example, distal portion 230 of carrier member 202 are more flexible than proximal portion 208. Such variability may be attained, for example, by annealing (FIG. 3A), tapering (FIG. 3B) or stepped reduction (FIG. 3C). In these and other embodiments, there preferably is a gradual transition from the more flexible distal end 304 to the stiffer proximal end 306 of the carrier member 202. It should be appreciated, however, that such a gradual transition in the noted direction may be particular to the exemplary application of cochlear implants and may vary differently in other applications.

Referring to FIG. 3A, stiffening element 302A is formed of, for example, glass or metal, which is annealed, i.e., subject to a process of heating and slow cooling to toughen and reduce brittleness. In the embodiment shown in FIG. 3A, longitudinally adjacent regions 308 (only one is identified for simplicity) of stiffening member 302A are subject to different annealing process, resulting in regions 308 having a different hardness. In particular, longitudinally successive regions 309 have incrementally greater or less flexibility, depicted in FIG. 3A by successively increasing and decreasing widths of regions 308.

Referring to FIG. 3B, stiffening element 302B is, in this illustrative embodiment, a unitary member that is tapered from its proximal end 306B toward its distal end 304B. The reduced volume of material along successive regions of stiffening element 302 results in a successively decreasing stiffness. It should be appreciated that the rate of taper will dictate the rate of change in flexibility of carrier member 202.

Referring to FIG. 3C, stiffening element 302C is an integrated element comprised of a plurality of elongate strips 310A-310D of differing lengths. Strips 310 may be formed of the same or different material, and may be manufactured to have the same or different stiffness. Strips 310 may be secured to each other or any manner now or later developed. As shown in FIG. 3C, stiffening member 302C has a stepped configuration, due to the different lengths of strips 310. As such, the stiffness provided by stiffening member 302C varies due to the cumulative contribution of each strip 310, which varies along its length. As one of ordinary skill in the art world would appreciate, strips 310 need not be arranged to form a continuous series of steps. For example, in embodiments in which the desired flexibility of carrier member 202 does not vary continuously, strips 310 may be configured such that, for example, strip 310B is longer than strip 310C.

Advantageously, stiffening member 208 provides electrode carrier member 202 with sufficient stiffness to allow it to be effectively inserted into cochlear 132, particularly once carrier member 202 encounters some resistance beyond the first turn of the cochlea. A further advantage of the variation in stiffness is to ensure that electrode assembly 200 is suitable for all cochlea sizes. Cochlea sizes, and therefore the basal length, from the round window to the lateral wall of cochlea 132, vary slightly between recipients. The basal length is generally a straight path and is usually in the order of approximately 4 mm to 7 mm. The more flexible distal end of stiffening member 208 ensures that the distal tip of the stiffening member does not impact with the fragile structures of the cochlea. Rather, the distal end deforms allowing carrier member 202 to curve whilst still ensuring the proximal region of the electrode array 200 does not buckle or deform. Preferably, the variable stiffness also ensures that carrier member 202 forms a gradual curve rather than a sharp bend that could result by having a sudden change in mechanical stiffness.

In addition to the embodiments illustrated in FIGS. 3A-3C, the variable stiffness can be achieved by utilizing any number of the following alone or in combination with each other or the embodiments described above: a plurality of stiffening members spaced at various pitches to provide a variable stiffness; use of different materials at various intervals along the length of stiffening member 208; varying dimensions of stiffening element 308 or its component elements, etc. It should also be appreciated that stiffening member 208 can be of any manufacturable cross-section, including round, square, rectangular, oval etc., and use any manufacturable method to provide variable stiffness along its length.

In alternative embodiments, stiffening element 208 extends further into carrier member 202, providing regions of enhanced stiffness where desired. It should be appreciated that the regions of stiffness in the embodiments illustrated in FIGS. 3A-3C, or otherwise, need not vary regularly or consistently.

This stiffening arrangement may be similar to that described in Australian Provisional Patent Application No. 2005904743, filed on 31 Aug. 2005, and U.S. Provisional Application No. 60/748,273 filed Dec. 8, 2005, which are hereby incorporated by reference herein in their entireties.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An apparatus, comprising:
a flexible elongate carrier member configured to introduce a therapeutic element into a recipient; and
a stiffening member, permanently embedded in and longitudinally extending through at least a first region of said carrier member, configured to decrease the flexibility of said first region so as to prevent deformation of said first region during implantation of said carrier member into the recipient.

2. The apparatus of claim 1,
wherein said apparatus is an electrode assembly of a prosthetic hearing implant,
wherein said therapeutic element comprises a plurality of electrodes configured to stimulate auditory nerves of a recipient's cochlea, and
wherein when inserted, said first region extends from an extracochlear location to a location just before a lateral wall of a first turn of the cochlea.

3. The apparatus of claim 1,
wherein said stiffening element is electrically conductive.

4. The apparatus of claim 1,
wherein said stiffness of said stiffening element longitudinally varies along at least a portion of said stiffening element.

5. The apparatus of claim 4,
wherein said longitudinally varying stiffness of said stiffening element is such that distal portions of said carrier member are more flexible than proximal portions of said carrier member.

6. The apparatus of claim 4,
wherein said stiffening element comprises a plurality of longitudinal regions each having a different stiffness.

7. The apparatus of claim 6,
wherein said successive longitudinal regions having incrementally increasing stiffness.

8. The apparatus of claim 4,
wherein said variable stiffness of said stiffening element is attained by annealing said stiffening element.

9. The apparatus of claim 4,
wherein said variable stiffness of said stiffening element is provided by a tapered surface of said stiffening element.

10. The apparatus of claim 4,
wherein said variable stiffness of said stiffening element is provided by a step-wise increase in thickness of said stiffening element.

11. The apparatus of claim 10,
wherein said stiffening element comprises a series of elongate strips a subset of which have different lengths.

12. The apparatus of claim 2, wherein said stiffening member is configured to provide said carrier member with sufficient stiffness thereby configuring said carrier member to be effectively inserted into the cochlea.

13. The apparatus of claim 1, wherein said medical device comprises:
a prosthetic hearing implant system.

14. The apparatus of claim 1,
wherein said medical device comprises a stimulating medical device; and
wherein said therapeutic element comprises a plurality of electrodes.

15. The apparatus of claim 14, wherein said stimulating medical device comprises one of a device selected from a group consisting of:
a cochlear implant; and
a neurostimulator; and
a cardiac pacemaker; and
a defibrillator.

16. The apparatus of claim 1, wherein said electrode assembly further comprises:
a holding member connected to a proximal end of said carrier member, said holding member configured to provide for improved handling by a person performing said implantation.

17. The apparatus of claim 16,
wherein said apparatus is an electrode assembly of a prosthetic hearing implant,
wherein said therapeutic element comprises a plurality of electrodes configured to stimulate auditory nerves of a recipient's cochlea, and
wherein said holding member is further configured to identify a current orientation of said electrode.

18. The apparatus of claim 1, wherein said electrode assembly further comprises:
a laterally-extending collar member connected to a proximate end of said carrier member, said collar member configured to prevent implantation of said apparatus beyond said collar.

19. The apparatus of claim 1, wherein said electrode assembly further comprises:
a profiled tip disposed at a distal end of said carrier member configured to facilitate atraumatic insertion of said carrier member.

20. The apparatus of claim 4, wherein said electrode assembly further comprises:
a lead longitudinally extending through said carrier member to electrically connected said electrodes with an external device.

21. The apparatus of claim 20, wherein said electrode assembly is configured to be implanted in a cochlea of a recipient, and wherein said external device is a receiver/stimulator unit of a cochlear implant.

22. The apparatus of claim 4,
wherein said carrier member comprises a longitudinally-extending medial surface configured to face the interior of a cochlea when inserted therein and an opposing longitudinally-extending lateral surface configured to face the external wall and bony capsule of the cochlea when inserted therein, and
wherein said plurality of electrodes are disposed on said carrier member such that a surface of each of said plurality of electrodes has a surface that is at least adjacent said medial surface of said carrier member when inserted in the cochlea.

23. The apparatus of claim 22,
wherein said plurality of electrodes each has a surface that is collocated with said medial surface of said carrier member.

24. A cochlear implant comprising:
a speech processor for processing received sounds to generate coded stimulation control signals;
a stimulator unit configured to generate stimulation signals in response to said control signals; and
an assembly comprising:
a flexible elongate carrier member configured to introduce a therapeutic element into a recipient; and
a stiffening member, permanently embedded in and longitudinally extending through at least a first region of said carrier member, configured to decrease the flexibility of said first region so as to prevent deformation of said first region during implantation into the recipient.

25. The cochlear implant of claim 24,
wherein when inserted, said first region extends from an extracochlear location to a location just before a lateral wall of a first turn of a cochlea.

26. The cochlear implant of claim 24,
wherein said stiffness of said stiffening element longitudinally varies along at least a portion of said stiffening element.

27. The cochlear implant of claim 24,
wherein said longitudinally varying stiffness of said stiffening element is such that distal portions of said carrier member are more flexible than proximal portions of said carrier member.

28. The cochlear implant of claim 24,
wherein said stiffening element comprises a plurality of longitudinal regions each having a different stiffness.

29. The cochlear implant of claim 28,
wherein said successive longitudinal regions having incrementally increasing stiffness.

30. The cochlear implant of claim 24,
wherein said variable stiffness of said stiffening element is attained by annealing said stiffening element.

31. The cochlear implant of claim 24,
wherein said variable stiffness of said stiffening element is provided by a tapered surface of said stiffening element.

32. The cochlear implant of claim 24,
wherein said variable stiffness of said stiffening element is provided by a step-wise increase in thickness of said stiffening element.

33. The cochlear implant of claim 32,
wherein said stiffening element comprises of a series of elongate strips a subset of which have different lengths.

34. The cochlear implant of claim 24, wherein said stiffening member is configured to provide said carrier member with sufficient stiffness thereby configuring said carrier member to be effectively inserted into a cochlea.

35. The cochlear implant of claim 24, wherein said assembly further comprises:
a holding member connected to a proximal end of said carrier member, said holding member configured to provide for improved handling by a person performing said implantation.

36. The cochlear implant of claim 24,
wherein said holding member is further configured to identify a current orientation of said electrode.

37. The cochlear implant of claim 24, wherein said therapeutic element comprises a plurality of electrodes disposed on the carrier member, said electrodes configured to stimulate auditory nerves of a recipient's cochlea.

38. The cochlear implant of claim 37,
wherein said carrier member comprises a longitudinally-extending medial surface configured to face the interior of the cochlea and an opposing longitudinally-extending lateral surface configured to face the external wall and bony capsule of the cochlea, and
wherein said plurality of electrodes are disposed on said carrier member such that a surface of each of said plurality of electrodes has a surface that is at least adjacent said medial surface of said carrier member.

39. The cochlear implant of claim 38,
wherein each of said plurality of electrodes has a surface that is collocated with said medial surface of said carrier member.

* * * * *